United States Patent
Le

(10) Patent No.: US 10,568,473 B2
(45) Date of Patent: Feb. 25, 2020

(54) PORTABLE EASYP URINAL

(71) Applicant: Khoa T Le, Aurora, CO (US)

(72) Inventor: Khoa T Le, Aurora, CO (US)

( * ) Notice: Subject to any disclaimer, the term of this patent is extended or adjusted under 35 U.S.C. 154(b) by 0 days.

(21) Appl. No.: 15/299,743

(22) Filed: Oct. 21, 2016

(65) Prior Publication Data

US 2017/0164795 A1 Jun. 15, 2017

Related U.S. Application Data

(63) Continuation-in-part of application No. 14/967,316, filed on Dec. 13, 2015, now abandoned.

(60) Provisional application No. 62/176,974, filed on Mar. 2, 2015, provisional application No. 62/125,882, filed on Feb. 2, 2015.

(51) Int. Cl.
A47K 11/12 (2006.01)

(52) U.S. Cl.
CPC .................................. *A47K 11/12* (2013.01)

(58) Field of Classification Search
CPC . A47K 11/12; A61F 5/453; A61F 5/44; A61F 5/4404; A61G 9/006; A61M 2039/1016; A61M 2039/1027; A61M 39/22; F16L 37/26; F16L 37/34
USPC ..................... 4/114.1, 144.1, 144.3
See application file for complete search history.

(56) References Cited

U.S. PATENT DOCUMENTS

| | | | | |
|---|---|---|---|---|
| 2,745,111 A | * | 5/1956 | Podmorski | A61F 5/4405 141/297 |
| 3,000,015 A | * | 9/1961 | Hart | A61G 9/006 4/144.3 |
| 5,285,532 A | * | 2/1994 | Sealy | A47K 11/12 4/144.1 |
| 5,331,689 A | * | 7/1994 | Haq | A47K 11/12 4/144.1 |
| 5,551,097 A | * | 9/1996 | Short | A61G 9/006 4/144.1 |
| 5,946,742 A | * | 9/1999 | Parker | B60R 15/04 4/458 |
| 6,212,691 B1 | * | 4/2001 | Heberer | A47K 11/12 4/144.1 |
| 6,493,883 B2 | * | 12/2002 | Jones | A47K 11/12 4/144.1 |

(Continued)

FOREIGN PATENT DOCUMENTS

KR 20130117132 A * 10/2013
KR 101406324 B1 * 6/2014

OTHER PUBLICATIONS

KR 101406324 B1 Translation.*
KR 20130117132 A Translation.*

*Primary Examiner* — Lauren A Crane
*Assistant Examiner* — William R Klotz

(57) ABSTRACT

A portable urinal includes a receptacle with a wide opening and an internal cavity which converges towards a tube neck and wherein a tube is attached to the tube neck. The tube is attached via a disconnect coupler to a container which can be sealed and separated from the tube. The receptacle is shaped to accommodate one or more of the male genitalia and the female genitalia. The portable urinal is designed to allow a user to urinate in restroom inaccessible locations without discomfort, without creating an odor, without chance of spilling bodily fluids, and without inappropriately exposing their body so that they can urinate in locations where other people may be present.

13 Claims, 13 Drawing Sheets

(56) References Cited

U.S. PATENT DOCUMENTS

| | | | | |
|---|---|---|---|---|
| 6,723,078 | B1* | 4/2004 | Pennington | A61F 5/451 |
| | | | | 604/327 |
| 6,732,384 | B2* | 5/2004 | Scott | A47K 11/12 |
| | | | | 4/144.1 |
| 8,046,848 | B2* | 11/2011 | Birbara | A47K 11/12 |
| | | | | 4/144.1 |
| 8,650,669 | B1* | 2/2014 | Kolter | A47K 11/12 |
| | | | | 4/144.1 |
| 9,603,737 | B2* | 3/2017 | Jenkin | A61F 5/453 |
| 2003/0140409 | A1* | 7/2003 | Johnson | B60R 15/04 |
| | | | | 4/458 |
| 2006/0277670 | A1* | 12/2006 | Baker | A61G 9/006 |
| | | | | 4/144.1 |
| 2012/0066825 | A1* | 3/2012 | Birbara | A47K 11/12 |
| | | | | 4/309 |
| 2012/0210503 | A1* | 8/2012 | Anzivino, Sr. | A61F 5/4556 |
| | | | | 4/144.3 |
| 2014/0310859 | A1* | 10/2014 | Brown | A61G 9/006 |
| | | | | 4/144.1 |
| 2016/0067132 | A1* | 3/2016 | Knowlton | A61G 9/006 |
| | | | | 4/144.3 |
| 2016/0095479 | A1* | 4/2016 | Jenkin | A61F 5/453 |
| | | | | 4/144.1 |

* cited by examiner

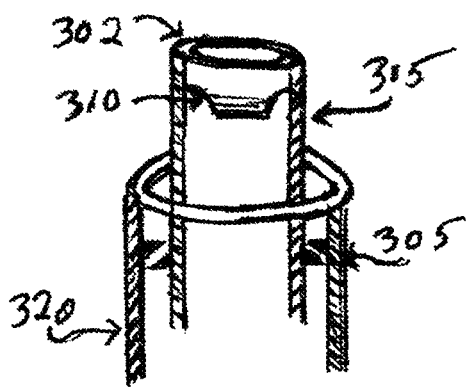
FIG. 11a
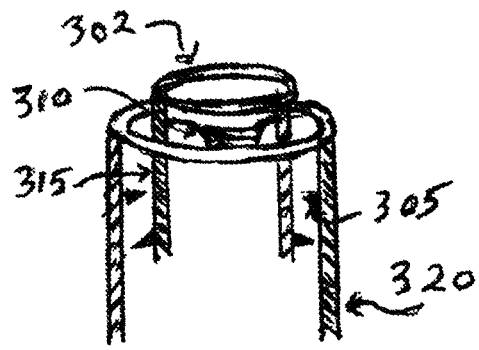
FIG. 11b
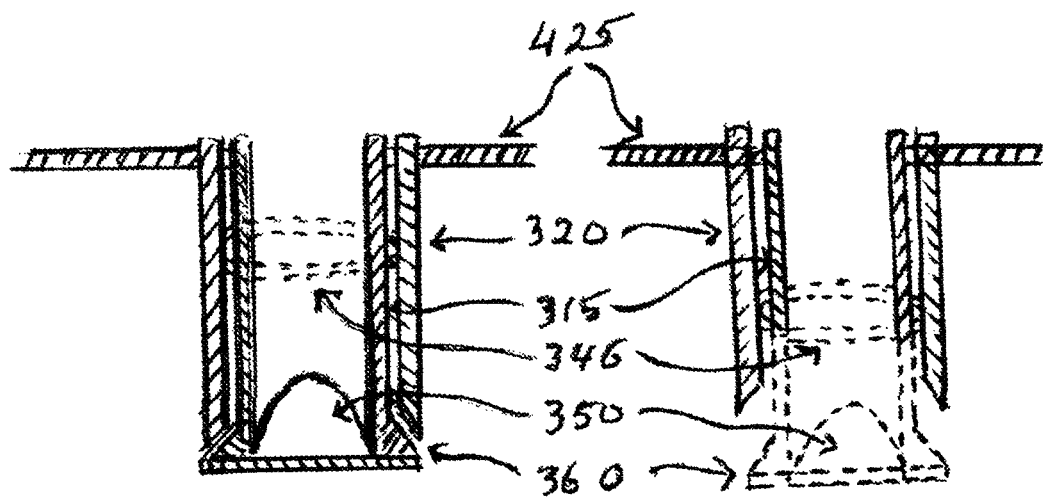
FIG 12a
FIG 12b

PORTABLE EASYP URINAL

CROSS-REFERENCE TO RELATED APPLICATIONS

This application is a continuation in part of patent application Ser. No. 14/967,316 filed on Dec. 13, 2015 and entitled "Portable EasyP Urinal" and claims priority thereto. Application Ser. No. 14/697,316 claimed priority to and incorporated by reference (1) U.S. Provisional Patent Application Ser. No. 62/176,974, filed 2 Mar. 2015 and entitled "THE 4NOS URINAL", and (2) Provisional Patent Application Ser. No. 62/125,882, filed 2 Feb. 2015 and entitled "Uholder on-the-go".

BRIEF DESCRIPTION OF THE FIGURES

FIG. 11*a* illustrates the close-up of the top end of the new flow control assembly in the closed state.

FIG. 11*b* illustrates the close-up of the top end of the new flow control assembly in the open state.

FIG. 12*a* illustrates the close-up of the bottom end of the new flow control assembly in the closed state.

FIG. 12*b* illustrates the close-up of the bottom end of the new flow control assembly in the open state.

DESCRIPTION OF THE PREFERRED EMBODIMENTS

The following description of the preferred embodiments of the invention is intended to enable someone skilled in the prior art to make and use this invention, but is not intended to limit the invention to these preferred embodiments.

First Preferred Embodiment

Figure 7:
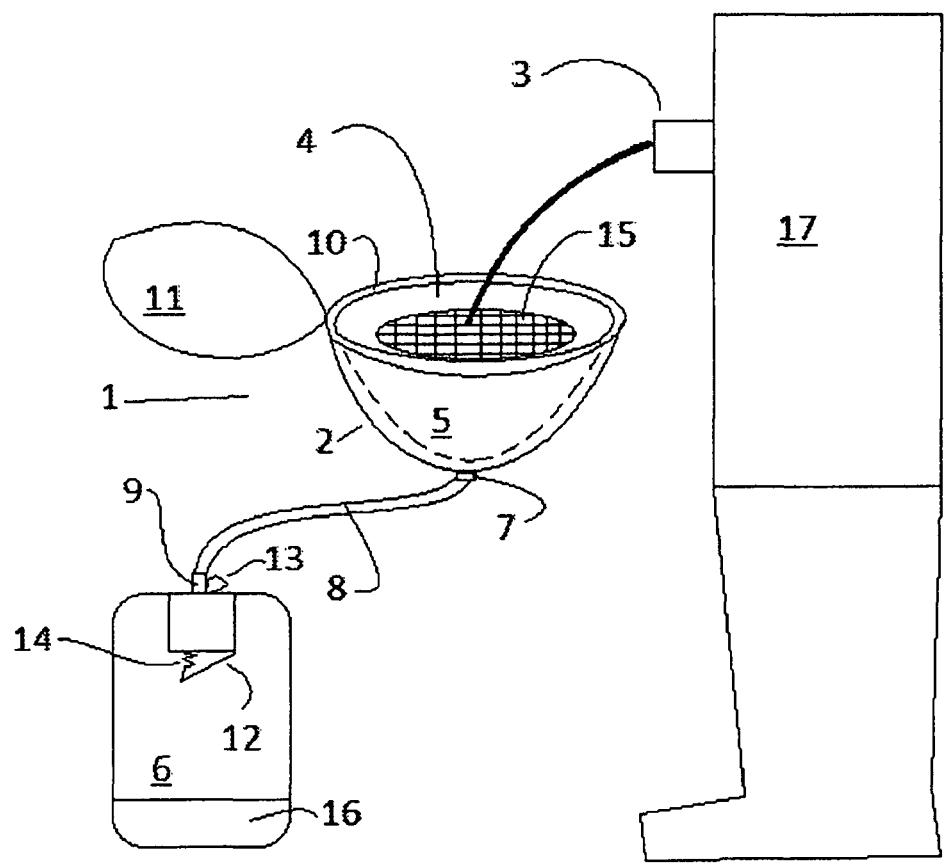
FIG. 7 is a schematic representation of the system of the first preferred embodiments, showing one variation of the device in use, and showing a specific variation of the components used with the system.

As shown in FIG. 7, the portable urinal 1 of the preferred embodiments comprises a receptacle 2 with a wide opening 4 and internal cavity 5, where the internal cavity 5 converges towards a tube neck 7, wherein a tube 8 is attached to the tube neck 7, wherein the tube 8 is attached via a disconnect coupler 9 to a container, where the container 6 can be sealed and separated from the tube, where the receptacle 2 is shaped to accommodate one or more of the male genitalia 3 and the female genitalia 3. The portable urinal 1 of the preferred embodiments is designed to allow a user 17 to urinate in a restroom inaccessible location without discomfort, without creating an odor, without chance of spilling bodily fluids, and without inappropriately exposing their body so that they can urinate in locations where other people may be present.

As shown in FIG. 7, the system of the first preferred embodiments has a receptacle 2 that is shaped to accommodate one or more of the male genitalia 3 and the female genitalia 3. The receptacle 2 has a wide opening 4 and internal cavity 5. In one variation, there may be separately produced portable urinal 1 *s* to accommodate the male and female genitalia 3 respectively. In one preferred variation, the female version of the portable urinal 1 may have one of a circular shaped wide opening 4, and an oval shaped wide opening 4 to the receptacle 2, and the opening to the receptacle 2 may be shaped to fit against the female genitalia 3. In one preferred variation, the male version of the portable urinal 1 may have an opening and cavity 5 shaped to fit around some or all of the male genitalia 3. In another preferred variation, the male version of the portable urinal 1 may have a receptacle 2 shaped to accept a stream of urine from a male user 17 from a distance of 2 inches. In a preferred variation, the rim of the wide opening 4 of the receptacle 2 is covered in an elastomeric material 10. The elastomeric material 10 may provide a softer, yielding surface to increase the comfort of the user 17 when using the portable urinal 1. This may be particularly advantageous for female users who may have to press the wide opening 4 of the receptacle 2 against the surface of their genitalia 3, or against the area surrounding their genitalia 3. In another preferred variation, the rim of the wide opening 4 of the receptacle 2 is covered in a silicone polymer material. The receptacle 2 may, however, have any suitable shape for capturing urine from a user. Male and female versions of the receptacle 2 may alternatively be identical, or have any suitable shape for interfacing with the needs of males and females. The rim of the wide opening 4 of the receptacle 2 may, however, have any suitable covering or protection, or may have no particular coating or protection at all.

As shown in FIG. 7, the portable urinal 1 preferably has a lid 11 that fits the wide opening 4 of the receptacle 2 and closes off the receptacle 2. This is done to prevent one or more of: dissemination of odors, leakage of bodily fluids, and unsanitary contact with the outside surfaces. After the use of the portable urinal 1, it is preferable that the portable urinal 1 can be closed and sealed in such a way that it can be transported safely and without undue obtrusion by the user. This may include being transported in a carry case sold with the portable urinal 1. It may also include being transported in a bag or a backpack of the user. The lid 11 preferably is pivotally attached to a hinge point molded to the receptacle 2 below the rim of the receptacle 2. In a preferred variation the lid 11 can be removed entirely from the hinge point by removal of the hinge pin. This may increase the comfort of using the device for female users. In a preferred variation, a flexible snap with a camming surface is attached to the lid 11 and engages a ledge on a latch lock molded to the receptacle 2 below the rim of the wide opening 4 of the receptacle 2, and on the opposite side of the wide opening 4 of the receptacle 2 from the hinge point. The hinge point may, however, be incorporated into the portable urinal 1 in any suitable manner. The lid 11 may, however, be removed in any suitable way from the hinge point. The lid 11 may, alternatively, not be removable from the hinge point. In another preferred variation, the lid 11 may be one or more of a snap on or friction fit without a pivot. In this preferred variation, the lid 11 may removably attach to the wide opening 4 of the receptacle 2 in a manner similar to a Tupperware lid. Alternatively, in this preferred variation, the lid 11 may removably attach to the wide opening 4 of the receptacle 2 in a manner similar to sealable polymer containers known to the art in hospital settings. The portable urinal 1 may, however, alternatively include no lid 11 at all for the receptacle 2. The lid 11 may, however, releasably fit to the receptacle 2 in any manner suitable for closing off the receptacle 2. Another sealing device may, however, be releasably fit to protect the inner surfaces of the receptacle 2.

As shown in FIG. 7, the container 6 is preferably coupled to the tube 8 by a disconnect coupler 9, allowing fluid 16 to flow from the tube 8 into the container 6 when the container 6 is not selectively sealed. There is preferably a movable sealing closure 12 attached to the container, which allows the opening of the container 6 to be sealed when desired. Preferably the movable sealing closure 12 seals the opening of the container 6 without further action from the user 17 when the user 17 disconnects the container 6 from the tube. This prevents one or more of spilling bodily fluids and dissemination of odors. Preferably the container 6 includes a button 13 that allows the user 17 to open the movable sealing closure 12 on the container 6 at any suitable time. In a preferred variation, there is an internally projecting tube 8 that projects into the interior of the container 6 and is coupled in fluid 16 communication with the opening of the container 6 such that no fluid 16 can enter the container 6 without going through the internally projecting tube. This structure may, however, have any suitable structure other than that of a tube. In a version of this preferred variation, the movable sealing closure 12 is pivotally attached to the internally projecting opening tube, and is designed to pivot into and out of a sealing position with the rim of the internally projecting opening tube. Preferably there is a spring 14 biasing the pivoting seal against the rim of the internally projecting opening tube, sealing the opening of the container 6 when the seal is not held away from the rim of the internally projecting opening tube 8 by external means. In one preferred variation, there is a control rod attached to a button, where the button 13 is attached to the end of the control rod and allows the user 17 to depress the control rod. The control rod is slideably mounted to the top of the container, and when it is depressed it forces the movable sealing closure 12 to pivot away from the rim of the internally projecting tube, opening the seal and allowing fluid 16 to flow from the opening of the container 6 into the container. In one preferred variation, a spring 14 biases the control rod upwards and the control rod is pivotally connected to the middle of the upper surface of the movable sealing closure 12, so that when the button 13 is not depressed the control rod moves upward and biases the movable sealing closure 12 against the rim of the internal opening of the internally projecting tube. In a preferred variation, when the disconnect coupler 9 coupling the tube 8 to the opening of the container 6 is attached so that the tube 8 is coupled to the container 6 and is in fluid 16 communication with the opening of the container, the attachment of the disconnect coupler 9 one or more of requires and causes the control rod to be forced downwards, opening the moving seal and allowing fluid 16 to flow from the tube 8 into the opening of the container 6 and through the internally projecting tube 8 into the container 6 interior. Preferably when the disconnect coupler 9 is disconnected such that the tube 8 is no longer coupled to the container, the control rod is one or more of allowed and caused to move upward, causing the movable sealing closure 12 to be biased against the rim of the internally projecting tube, sealing the opening of the container 6 and preventing one or more of odors and bodily fluids from escaping the container. In an alternative embodiment, the movable sealing closure 12 may slide upwards and downwards on a slidable mount. In an alternative embodiment, the movable sealing closure 12 may seal against any internal surface. In an alternative embodiment, the movable sealing closure 12 may seal with an o-ring against the walls of an interior surface. In an alternative embodiment, the movable sealing closure 12 may be mounted on the interior of the container. In an alternative embodiment, the movable sealing closure 12 may be biased into sealing the opening to the container 6 when the tube 8 is disconnected by any suitable means. In an alternative embodiment, the seal is not biased by any physical means, and is moved into a position sealing the opening to the container 6 by the action of disconnecting the tube 8 from the container. In an alternative embodiment, the control rod may not include a button 13 and may be moved by any suitable means. In an alternative embodiment, the seal may be an elastomeric material 10 designed to seal any opening using the elastic rebound of the material when the tube 8 is disconnected from the container. In an alternative embodiment, the container 6 may not contain a movable sealing closure 12 and may use any form of prior art lid. In an alternative embodiment, the tube 8 is connected to the container 6 via one or more of threads and a friction neck. The tube 8 may, however, be connected to the container 6 by any suitable means.

Figure 8:
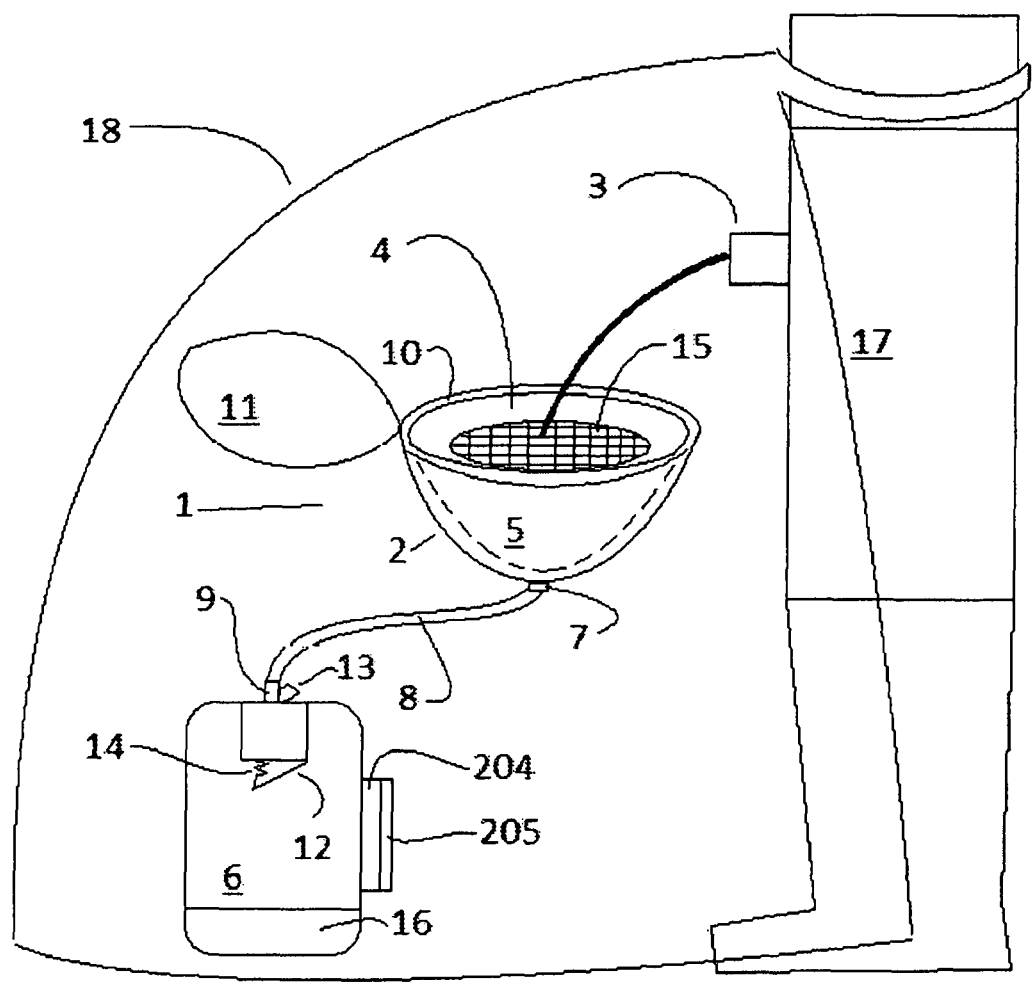
FIG. 8 is a schematic representation of the system of the first preferred embodiments, showing one variation of the device in use, and showing a specific variation of the components used with the system, where a storage compartment and storage compartment lid are included, and where a privacy garment is also shown in use to protect the privacy of the user.

As shown in FIG. 8, the portable urinal 1 is preferably sold as a system where the system also includes a fabric covering that covers one or more of the portable urinal 1 and exposed body parts of the user 17 involved with the use of the portable urinal 1. This fabric covering is preferably intended to protect one or more of the privacy of the user 17 while using the portable urinal 1, and the exposure to unpleasant sights of any other persons within sight of the user 17 while the user 17 uses the portable urinal 1. The portable urinal 1 may be used by users in developing countries. The portable urinal 1 may also be used in circumstances where users do not have the time or opportunity to use a toilet or seek privacy before urinating. The fabric covering is intended as a part of the system with the portable urinal 1 to allow the acceptable use of the portable urinal 1 in situations where the user 17 may have to urinate in an otherwise inconvenient location or at an otherwise inconvenient time. It is not currently feasible for a person to urinate in a location where other people may be present. It is also not currently feasible for a person to urinate in a location that may be used by other people but where a standard toilet is not accessible. There is no current way for a person to urinate in such locations without causing one or more of: obtrusive odors, unsanitary conditions, risk of spilling of bodily fluids, risk of splashing of bodily fluids, and visual exposure that may be considered inappropriate. The features of the portable urinal 1 are preferably designed to allow urination in conditions for which there has been a long standing but unsatisfied need by addressing these issues. The system of the preferred embodiments may, however, be sold simply as a portable urinal 1 with no additional items. The system of the preferred embodiments may, however, be packaged or sold in any suitable manner and with any suitable items which assist in the intentional use of the device.

As shown in FIG. 7, the portable urinal 1 of the preferred embodiments preferably includes one or more of a mesh 15 and a sieve 15 mounted inside the cavity 5 of the receptacle 2. The one or more of a mesh 15 and a sieve 15 preferably breaks up a stream of urine to prevent the stream of urine from directly striking the inside of the receptacle 2 in a way that causes urine to splash back towards the wide opening 4 of the receptacle 2. The one or more of a mesh 15 and a sieve 15 is preferably removably mounted inside the cavity 5 of the receptacle 2, allowing for cleaning. The one or more of a mesh 15 and a sieve 15 is preferably given a concave shape, with the concavity facing towards the wide opening 4 of the receptacle 2. The one or more of a mesh 15 and a sieve 15 may, however, be shaped in any suitable manner and may, however, be mounted to the receptacle 2 in any suitable way and in any suitable location. The system of the preferred embodiments may, however, not include one or more of a mesh 15 and a sieve.

The system of the preferred embodiments is preferably designed to overcome issues with prior art urinals so that a user 17 can urinate in locations that may be used by other people. These issues can include one or more of: odors from the urinal, odors from urination, splashing of bodily fluids, spilling of bodily fluids, inappropriate visual exposure. Where inappropriate visual exposure can include but is not limited to one or more of the following: visual exposure of the user's body parts not accepted by societal norms, visual exposure of the user's body parts in violation of local laws, visual exposure of the portable urinal 1 device, visual exposure of the urination process, visual exposure of the user's body in ways that offends nearby individuals, visual exposure of the device in ways that offends nearby individuals, and visual exposure of the urination process in ways that offends nearby individuals. In a preferred variation, the device is designed to avoid all of the problems with prior art urinal devices at once, including inappropriate visual exposure, release of bodily fluids outside the portable urinal 1 device, and release of odors. The system of the preferred embodiments may, however, be used and designed for any suitable purpose and any suitable benefits.

The system of the preferred embodiments is preferably constructed of materials that avoid one or more issues including corrosion, odors from use, and creation of unsanitary conditions. Urine can be corrosive towards some materials, and preferably the materials the portable urinal 1 is constructed of avoid corrosion from urine. Exposure to urine can lead to odors from materials which one or more of: directly trap materials, allow the growth of bacteria, are chemically affected by urine resulting in odors. Exposure to urine can also cause unsanitary conditions in some materials. Preferably the system of the preferred embodiments is made of medical grade materials preferably these medical grade materials address all of these issues. In a preferred variation the system of the preferred embodiments is made mostly from medical grade polymers selected to avoid these issues. The system of the preferred embodiments may, however, be made of any suitable materials.

The portable urinal 1 of the first preferred embodiments, wherein the releasable coupler 9 that releasably couples the container 6 and the tube 8 further includes a closure adapted to selectively seal the opening of the releasable coupler 9 when the tube 8 is removed from the coupler. In a preferred variation, a spring 14 loaded sealing closure 202 is slidably mounted inside the releasable coupler, and when the releasable coupler 9 is disconnected from attachment to one or more of the tube 8 and the mount attached to the container, the sliding closure is biased into a sealing position to close the coupler. The releasable coupler 9 may, however, include any suitable form of closure. The releasable coupler 9 may, however, include no closure.

The portable urinal 1 of the first preferred embodiments, wherein at least two guide collars 112 are attached to the container, wherein the at least two guide collars guide the motion of at least one control rod.

The portable urinal 1 of the first preferred embodiments, wherein the portable urinal 1 is adapted to be placed on a supporting surface below a user, wherein the receptacle 2 is adapted to be supported with the opening of the receptacle 2 facing upward, wherein the receptacle 2 is adapted to be supported with sufficient stability to prevent the receptacle 2 from being moved from its support position by a stream of urine, wherein the user 17 can urinate into the portable urinal 1 without holding the portable urinal 1 and without attaching the portable urinal 1 to the user's clothing and without attaching any component of the portable urinal 1 to the user's body.

The portable urinal 1 of the first preferred embodiments, further comprising a storage compartment 204 attached to the container, wherein the storage compartment is attached to the exterior of the container, wherein a movable lid 205 is attached to the container 6 and adapted to allow the storage compartment to be closed to contain items placed in the storage container.

The portable urinal 1 of the first preferred embodiments, wherein the releasable coupler 9 is attached to at least one of A) a cap removably attached to the container 6, and B) the wall near the top of the container 6.

Second Preferred Embodiment

Figure 1:
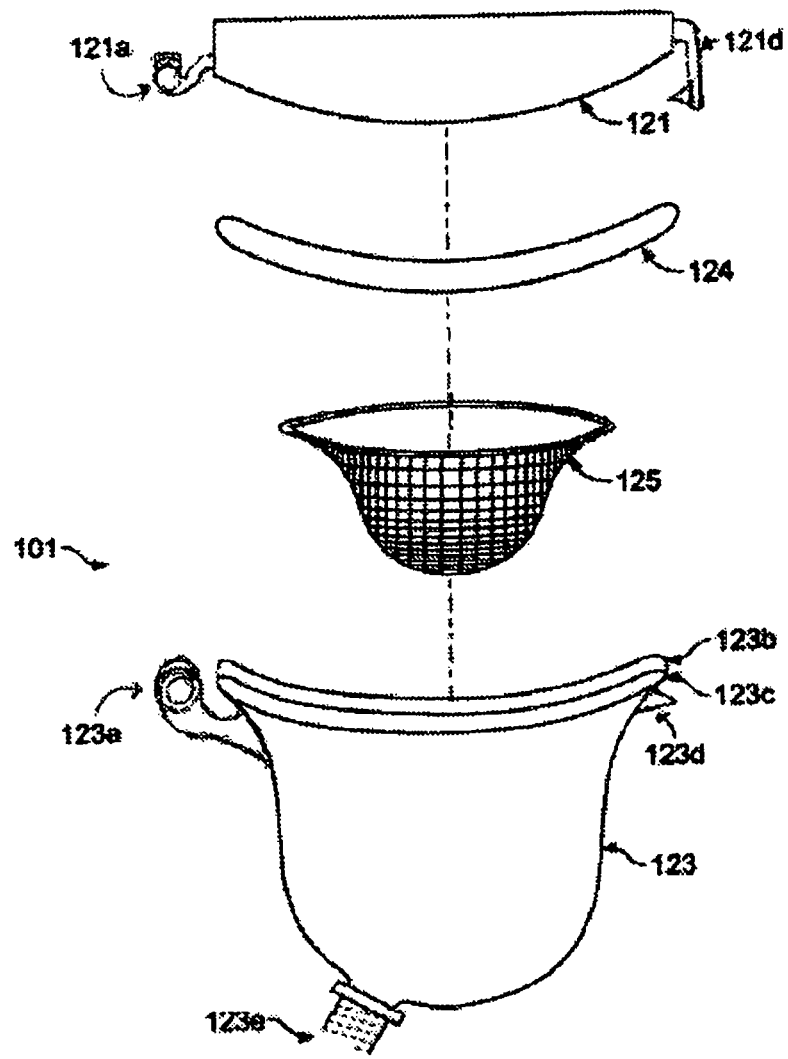
FIG. 1 is an exploded view of the receptacle of the second preferred embodiments.

FIG. 1 illustrates an exploded view of a receptacle 101 of the second preferred embodiment. In a variation of the second preferred embodiment, there may be two or more variations of the receptacle. The receptacle s may be shaped according to female and male genitalia. In another variation, a receptacle for children may be smaller. In another variation, the receptacle may be designed for use with male, female and children users. It is structured according to the female and male genitalia, but preferably many of the design features of the receptacle are intended for acceptable use with the female anatomy.

The portable urinal 100 includes a receptacle 101, where the contour is shaped to accommodate both female and male genitalia. In one variation, the receptacle 101 is shaped in the front to fit a female user's genitals, with a rear portion rounded for male genitalia. The receptacle 101 may have a lid 121 and a receptacle body 123. In a preferred variation, the receptacle body 123 is oval-shaped at its rim 123b with an enclosed wall extending from the rim 123b downward and converging to a neck 123e. In a preferred variation, the receptacle body 123 has enough space inside to fit a sieve 125. In another preferred variation, a rim projection 123c at the base of the rim 123b. The rim projection may be 123c is curved out and bent downward to provide a snap-fit with the edge of the lid 121. A soft silicone polymer cushion 124 may be included in a preferred variation, where the soft silicone polymer cushion 124 follows the contour of the rim 123b of the receptacle body 123 and is firmly fixed to the rim 123b. In a preferred variation, both the rim 123b and the soft silicone polymer cushion 124 may be shaped according to the female genital. The lid 121 may be built according to the contour of the receptacle body 123 and is preferably designed have a fluid/air tight closure with one or more of the receptacle body 123 and the rim projection 123c. In a preferred variation, the lid 121 may have a metal rod 121a secured to the rear of the lid 121 at one side and a tube 123a secured to the back of the receptacle body 123 below the rim projection 123c. When the rod 121a slides inside the tube 123a, there is also a one or more of a latch positioned at the other end of the tube 123a, and a threaded nut that may be threaded onto the end of the rod, where the rod end has been threaded, to stop the rod 121a from sliding out of the tube 123a. Both the lid 121 and the receptacle body 123 may have a female 123d and male 121d cam and catch structures for locking the lid to the receptacle. The fitting 123e is designed to transfer urine collected at the receptacle body 123 to the tube 102 and is couple to the cap 116 of the tube 102. The structure of the second preferred embodiment may, however, have any suitable construction and any suitable shape, and may include any suitable features as outlined in the first preferred embodiment.

In a preferred variation, to solve the problem of urine splash back and to allow female and male users to urinate with ease and comfort, a sieve 125 may be removably attached inside the receptacle. In a preferred variation, the sieve 125 may be a mesh screen made of stainless steel with its rim seated inside the midsection of the receptacle body 123. The sieve 125 is designed to break up urine streams before they hit the inner wall. The sieve may, however, have any suitable construction. Alternatively there may be no sieve.

Figure 2:
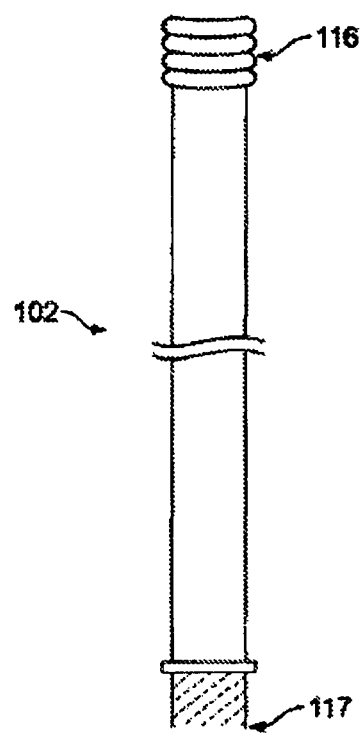
FIG. 2 is a view of the tube of the second preferred embodiments.

FIG. 2 illustrates the front perspective view of the tube 102. In a preferred variation, the cap 116 of the tube 102 connected to the fitting 123e of the receptacle body 123 and the fitting 117 of the tube 102 connected to the adapter 103a of the tube 103 is designed to transfer urine collected at the receptacle 123 through the tube 102 to the tube 103. The tube may be made of medical grade polymer to ensure elasticity and smooth flow without being kinked, collapsible or backing up of urine flow. Both the cap 116 and the fitting 117 may be made of medical grade plastic. The cap 116 may have a rubber seal inside to stop leakage and dissemination of odor. These structures may, however, have any suitable design and coupling, and may be made of any suitable materials as shown in the first preferred embodiment.

Figure 3:
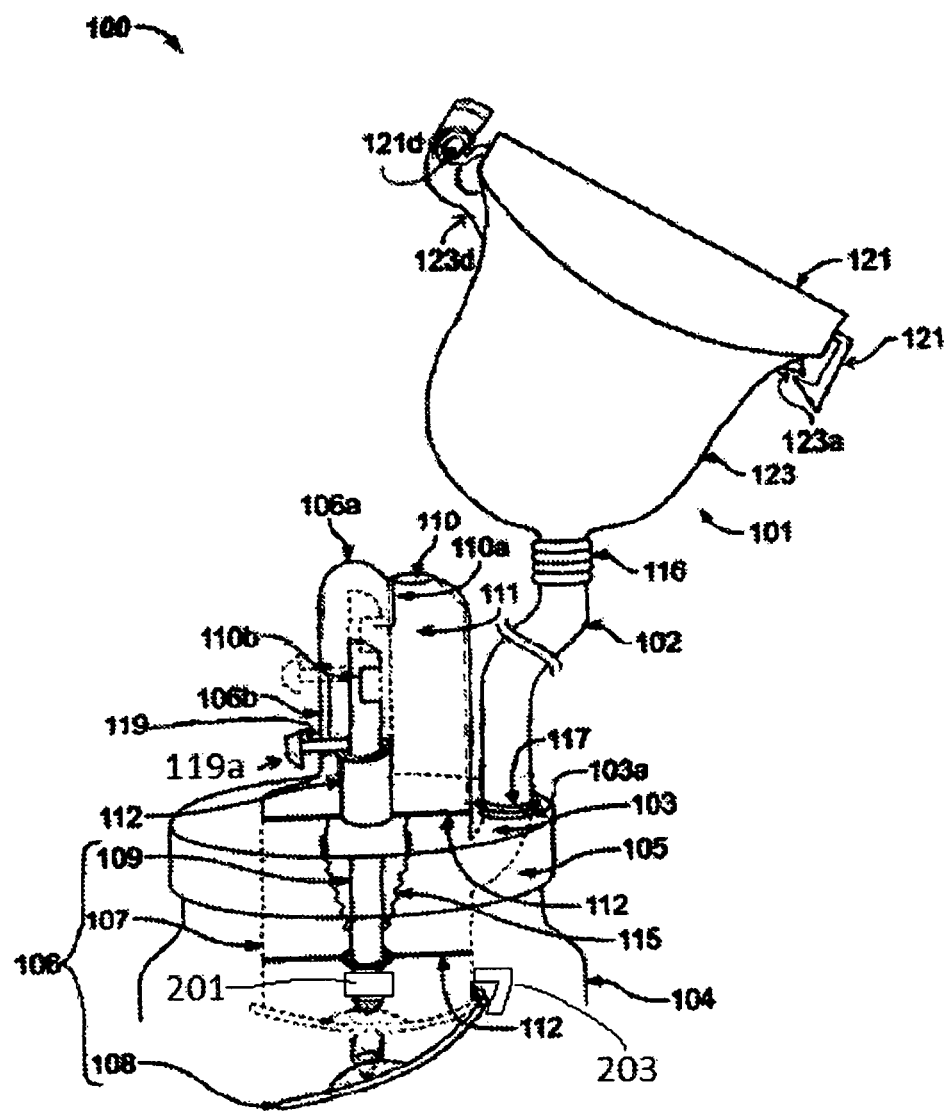
FIG. 3 is a schematic illustration of the system of the second preferred embodiments.

FIG. 3 illustrates an internal perspective view of the portable urinal 100. The portable urinal 100 disclosed herein comprises a receptacle 101, a tube 102, a tube 103, a container cap 105 and a flow control assembly 106. The receptacle 101 composed of the lid 121 and the receptacle body 123 is designed to receive urine from a user. The cap 116 of the tube 102 is connected to the fitting 123e of the receptacle 123 and its fitting 117 connected to the adapter 103a of the tube 103 designed to transfer urine collected at the receptacle 123 to the tube 103. The tube 103 is designed to transfer urine from the tube 102 to the container 104. The cap 105 closing and opening the container 104 is designed to position the flow control assembly 106. The flow control assembly 106 comprises a wall support 111, guide support structures 112, a control rod 109 and a cylinder 107. These structures may, however, have any suitable design and coupling, and may be made of any suitable materials as shown in the first preferred embodiment.

The container cap 105 is round and large enough to house an adapter 103a of the tube 103, a guide support 112 which is part of the top of the container cap 105 and the flow control assembly 106. The container cap 105 has threads to open and close the container 104. The container cap 105 has, some protruding edges for a good grip for easy closing and opening. The container cap 105 has a rubber seal inside to stop leakage and dissemination of odor. These structures may, however, have any suitable design and coupling, and may be made of any suitable materials as shown in the first preferred embodiment.

The tube 103 may be positioned outside the guide support 112 on the container cap 105. It has the adapter 103a sealedly positioned on the container cap 105 at one end and connected to a small circular cross section of the cylinder 107 at the other. The adapter 103a may be connected to the fitting 117 of the tube 102 designed to transfer urine from the tube 102 to the tube 103. To stop dissemination of odor or urine in the container 104 from getting out a protective fitting may be designed to seal the adapter 103a of the tube 103 with a small cap activated by a spring to close the adapter 103a. These structures may, however, have any suitable design and coupling, and may be made of any suitable materials as shown in the first preferred embodiment.

The flow control assembly 106 comprises guide supports 112, a wall 111, a control rod 109 and a cylinder 107. The flow control assembly 106 controls the operation of the portable urinal 100. These structures may, however, have any suitable design and coupling, and may be made of any suitable materials as shown in the first preferred embodiment.

There may be a plurality of guide supports 112. The first guide support 112 mentioned here is part of the top of the container cap 105. The guide support 112 has, a round shape and has, a circular cross section for the control rod 109 to pass through. The guide support 112 has sufficient space for the wall 111 to be positioned on. The circular cross section of the guide support 112, the base of the round housing 106a and the cylinder 107 are of the same dimension. The base of the round housing 106a, the top open end of the cylinder 107 are sealed with the outer circular edge of the circular cross section of the guide support 112. The guide support 112 positions the control rod 109 and provides a guide way for the control rod 109 to traverse in a vertical direction. These structures may, however, have any suitable design and coupling, and may be made of any suitable materials as shown in the first preferred embodiment.

The wall 111 may be sealedly seated between the inner circular edge of the circular cross section and the outer circular edge of the guide support 112 designed to facilitate the working of the control rod 109. On the upper flat top of the wall 111 may be positioned, a button 110 which may be connected to a latch 110a. These structures may, however, have any suitable design and coupling, and may be made of any suitable materials as shown in the first preferred embodiment.

The circular cross section of another guide support 112 may be of the same dimension as that of the guide support 112 just mentioned above. The circular cross sections of the two guide supports 112 are perfectly aligned. One open end of this guide support 112 may be sealedly connected to the circular cross section of the other guide support 112. The control rod 109 passes through the other open end and the circular cross section of the guide support 112. The guide support 112 also sealedly connected to the wall 111 without any interference with the vertical motion of the control rod 109 may be also designed to position the control rod 109 and to provide a guide way for the control rod 109 to traverse in a vertical direction. These structures may, however, have any suitable design and coupling, and may be made of any suitable materials as shown in the first preferred embodiment.

The control rod 109 can be in a number of shapes and forms. But for the purpose of illustration only the control rod 109 may be, round and small in size. Its length is roughly from the top of the wall 111 to the edge of the bottom open end of the cylinder 107, positioned within the guide supports 112, the cylinder 107 and in front of the wall 111 having a switch rod 119, a switch button 119a, a latch 110b and a bent-out rod 109a. The control rod 109 is supported by the wall 111 and the guide supports 112. A small portion at the top of the control rod 109 is curved downward to help the latch 110a to have an easy engagement with the upper edge of a lock 110b positioned behind the top portion of the control rod 109 for a locking mode. The switch button 119a positioned outside the round housing opening 106b is connected to the switch rod 119 which is connected to the control rod 109 and extends a little bit beyond the round housing opening 106b. The switch button 119a is installed and designed to operate the portable urinal 100. The lock 110b has a decent depth and perfectly aligned with the latch 110a for a smooth locking engagement. Both ends of the small bent-out rod 109a are sealedly connected to the bottom end of the control rod 109. A substantially sufficient weight is built into the control rod 109 in such a way that the control rod 109 has the adequate weight needed to pull down the control rod 109 as well as open the cap 108 of the bottom open end of the cylinder 107 at the same time once the control rod 109 is automatically released vie the button. The addition of the substantially sufficient weight is designed to achieve an automated mode of operation. The control rod 109 is designed to drop down or pull up and contact the cap 108 to open and close the bottom open end of the cylinder 107 when the control rod 109 is automatically released by a push button 110 or manually operated by the user to transfer urine from the receptacle 101 to the container 104 and to stop urine in the container 104 from getting out. The control rod 109 helps the flow control assembly 106 to control the operation of the portable urinal 100. These structures may, however, have any suitable design and coupling, and may be made of any suitable materials as shown in the first preferred embodiment.

The round housing 106a with its base sealedly connected to the outer circular edge of the circular cross section of the guide support 112 which is part of the top of the container cap covers a portion of the flow control assembly 106 on the container cap 105 except the button 110 and is exposed with, a round housing opening 106b. At the low end of the opening 106b the switch rod 119 rests upon the guide support 112. This indicates the portable urinal 100 is in use. At the high end of the opening 106b the switch rod 119 stops. This indicates the portable urinal 100 is not in use. The drop distance of the switch rod 119 from the high end to the low end of the opening 106b is called the predefined limit indicating a drop allowance limit for the control rod to drop resulting in a substantially sufficient width of the opening by the cap 108. Inside and toward the top of the round housing 106a there is built in a structure to gradually move the top of the control rod 109 from the low end to the high end of the opening 106b where the top of the control rod 109 barely touches the front of the wall 111, which helps the latch 110a to engage with the lock 110b easily. This structure does not interfere in any way with the control rod 109 dropping down once automatically released by the button 110. From the high end this opening 106b goes straight down, not curved accordingly with the contour of the round housing 106a and bent out to meet the contour of the base of the round housing 106a. The base of the round housing 106a has threads for the circular protective cap to be screwed onto to cover tight the round housing 106a to prevent an accidental opening and water or cleaning solutions from getting inside the flow control assembly 106 during the cleaning process. These structures may, however, have any suitable design and coupling, and may be made of any suitable materials as shown in the first preferred embodiment.

The cylinder 107 may be in any shapes and forms. The cylinder 107 is positioned beneath the container cap 105 with its top open end sealed with the outer circular edge of the circular cross section of the guide support 112 houses, a small circular cross section connected to one end of the tube 103, an rubber seal 115, a guide support 112, and a cap 108. The cylinder 107 serves as a urine pathway designed to transfer urine from the tube 103 to the container 104. These structures may, however, have any suitable design and coupling, and may be made of any suitable materials as shown in the first preferred embodiment.

The rubber seal 115 wraps around the lower part of the control rod 109 near the guide support 112 at one end and around the circular cross section of the guide support 112 at the other in a fluid tight enclosure. The rubber seal 115 provides sealing between the lower part of the control rod 109 and the guide support 112, thus preventing leakage of urine in the container 104 through the circular cross section of the guide support 112. These structures may, however, have any suitable design and coupling, and may be made of any suitable materials as shown in the first preferred embodiment.

The guide support 112 inside the cylinder 107 has a circular cross section perfectly aligned with the circular cross section of the guide support 112 above it in the same dimension with two rods on both sides of its circular cross section connected to the inner wall of the cylinder 107. This guide support 112 also positions the control rod 109 and provides a guide way for the control rod 109 to traverse in a vertical direction. These structures may, however, have any suitable design and coupling, and may be made of any suitable materials as shown in the first preferred embodiment.

The cap 108 of the cylinder 107 may be secured by a hinge at one outside edge of the bottom open end of the cylinder 107. The control rod 109 may be in contact communication with the cap 108 to open and close the bottom open end of the cylinder 107 automatically via the button 110 or manually operated by the user to transfer urine from the receptacle 101 to the container 104 and to stop leakage from the container 104. There may be a rubber seal on the inner surface of the cap 108 for a fluid/air tight with the bottom open end of the cylinder 107 to prevent urine in the container 104 from getting inside the cylinder 107. There may be a bent-out rod 108a at the center area of the inner surface of the cap 108. This rod has one end sealed to the inner surface of the center area and the other end may be open. This open end may be designed to interlock with the bent-out rod 109a with both of its ends sealedly connected to the bottom end of the control rod 109. As soon as this open end may be interlocked with the bent-out rod 109a this open end may be pushed into a slot of the cap 108 with a notch inside the slot to lock it. When the cap 108 may be closed fluid/air tight with the bottom open end of the cylinder 107 both bent-out rods 108a and 109a hold together tight and are interlocked. These structures may, however, have any suitable design and coupling, and may be made of any suitable materials as shown in the first preferred embodiment.

Figure 4A:
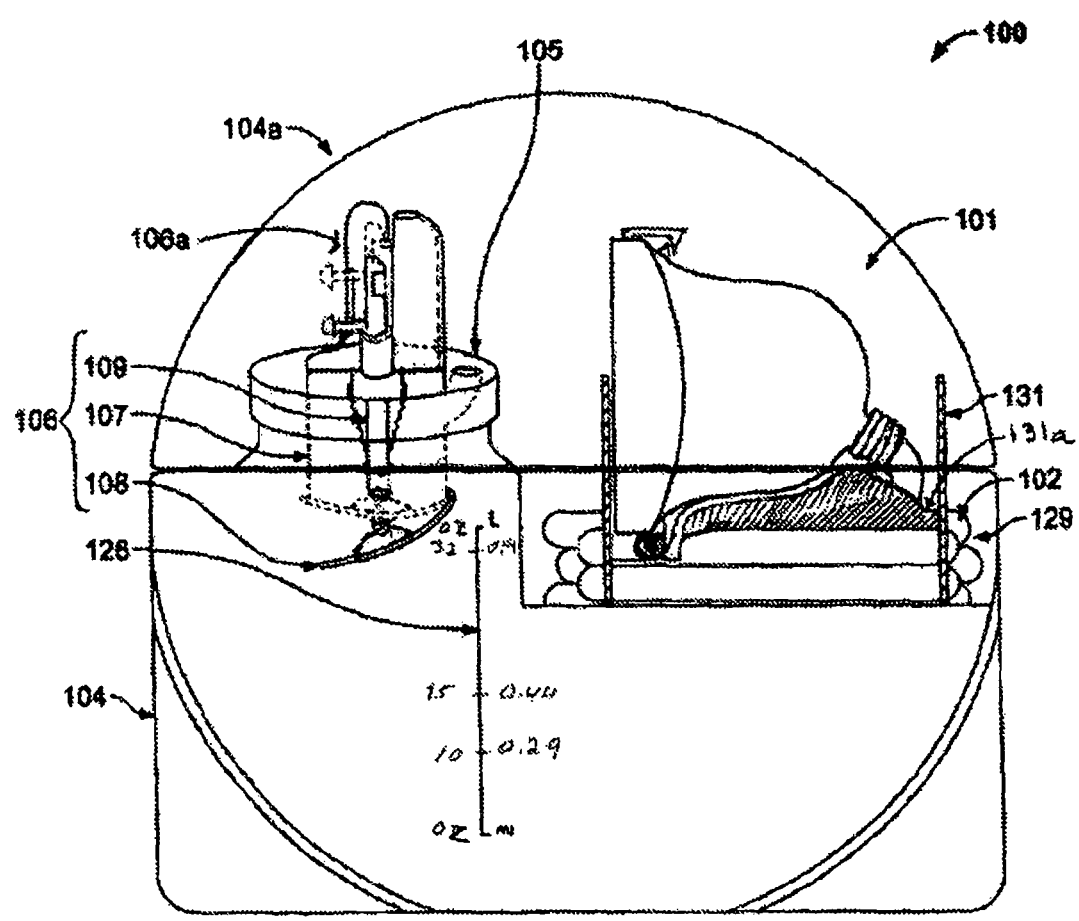
FIG. 4*a* illustrates the side view of a variation of the second preferred embodiments of the flow control assembly and the storage compartment structure in a compact model for both women and men, where the system is held in a closed state.
Figure 4B:
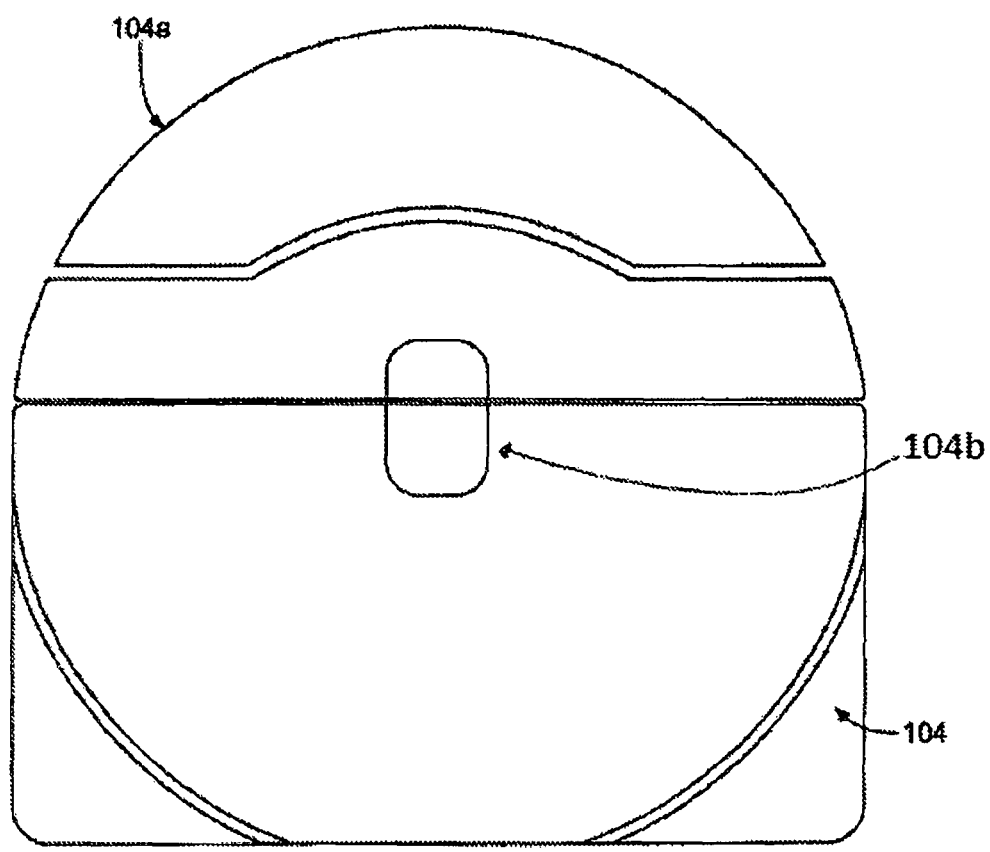
FIG. 4*b* illustrates the side view of a variation of the system of the second preferred embodiments, where the compact model is held in a closed state.

FIG. 4A illustrates the side view of the flow control assembly 106 and the storage compartment 129 and FIG. 4B illustrates the side view of the compact model in a closed state. With reference to the detailed description of FIG. 3, the flow control assembly 106 may be positioned through the container cap 105 and its corresponding detailed description. The storage compartment 129 partly hidden below the container shoulder has a rack 131 for the urine transmission tube 102 to wrap around and a molded slot 131a for the receptacle 101 to be seated. This may be the compact model for women and men including children. It may be sized and designed to hold urine for a day's use. These structures may, however, have any suitable design and coupling, and may be made of any suitable materials as shown in the first preferred embodiment.

The portable urinal 100 has a roughly half round cover 104a on top and a partly half round on the surface and partly rectangular in the background at the bottom. For the circular face, the edge and the front are rounded smoothly and uniformly from top to bottom, from edge to edge and from edge to the center of the depth except a small portion cut off at the bottom. Therefore the actual depth may be reduced to a smaller size. This makes the portable urinal 100 looks somewhat smaller without sacrificing its operation and volume holding. There are two rims along the edges of the circular portions at the lower part of the container 104. These structures may, however, have any suitable design and coupling, and may be made of any suitable materials as shown in the first preferred embodiment.

There are two plastic hinges firmly secured to the back of the cover 104a and the upper edges of the container 104. Also there are one half ring horizontally embedded behind the top portion of the container 104 for hanging or holding. There are also two half rings embedded on both top ends of the shoulders of the container 104 on both sides. In front of the portable urinal 100 there may be a lock 104b in the middle with a plastic covered metal bar secured to the front of the cover 104a and a hook positioned on the front of the container 104 just below the plastic covered metal bar. When the hook engages firmly with the plastic covered metal bar and may be pulled down the cover 104a and the container 104 are in a locking mode. Both the plastic covered metal bar and the hook are inside the lock 104b. The container 104 has a volume marking 128 to alert the user when may be the good time to drain out the urine through the removal of the container cap 105 or a release opening in the rear of the container 104. These structures may, however, have any suitable design and coupling, and may be made of any suitable materials as shown in the first preferred embodiment.

Figure 5:
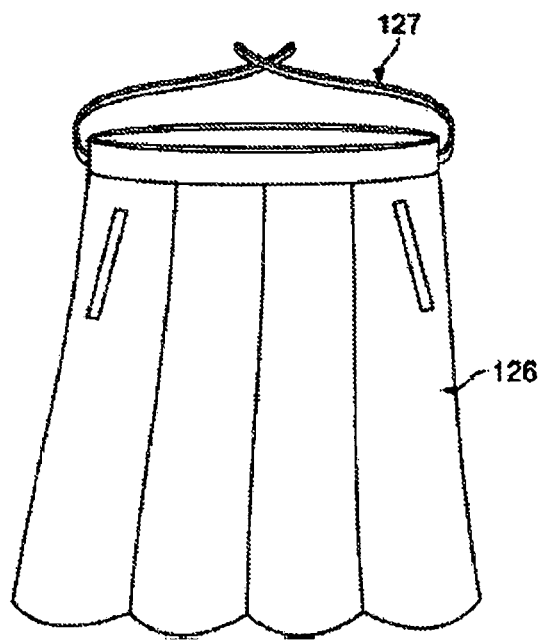
FIG. 5 illustrates a preferred variation of the privacy garment of the second preferred embodiments.

FIG. 5 illustrates a front perspective view of the privacy garment 126. In an embodiment, the portable urinal 100 further comprises a privacy garment 126 designed to be wound around the user's waist to protect the user's privacy when the user excretes urine into the receptacle body 123. In an embodiment, the privacy garment 126 comprises two openings for the user to access the receptacle body 123. The privacy garment 126 may be made of fabric with an elastic band sewn behind its waistband whose ends have strings 127 to be tied around the torso. There may be also a set of ties half way down along the cover edges for an extra tie in case of strong winds. These structures may, however, have any suitable design and coupling, and may be made of any suitable materials as shown in the first preferred embodiment.

Figure 6:
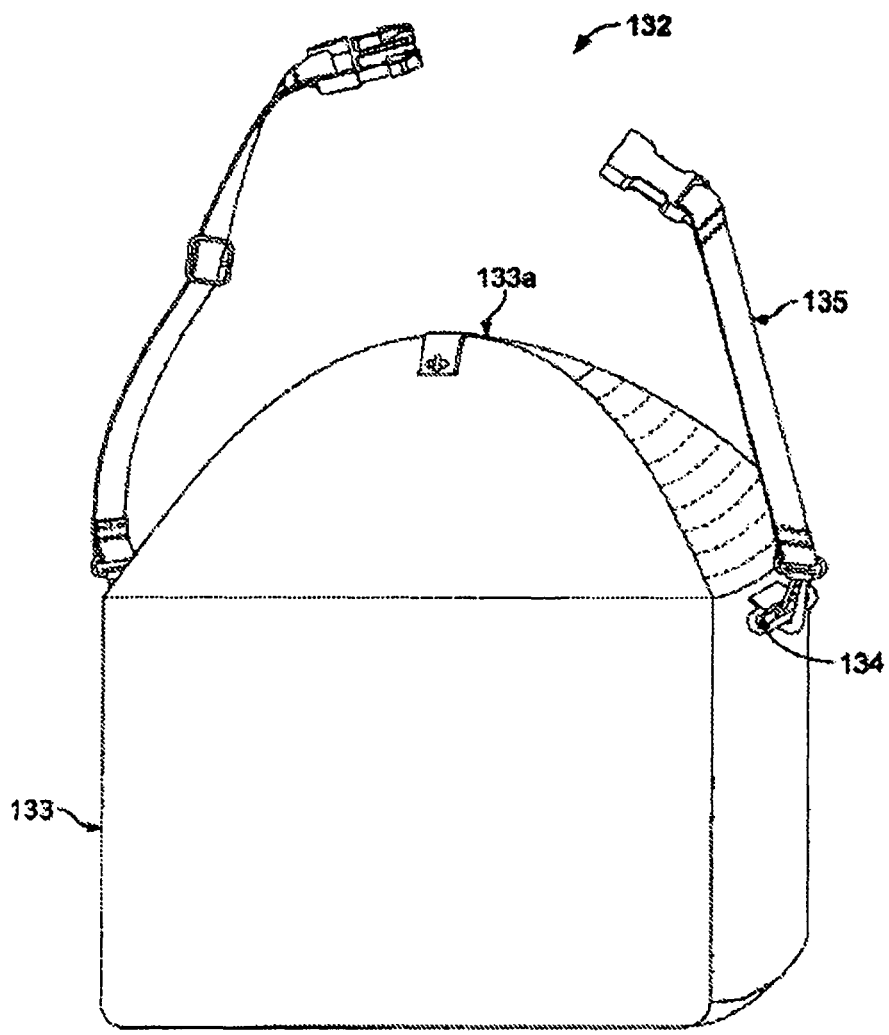
FIG. 6 illustrates a preferred variation of the front view of the carrying pouch from the second preferred embodiments.

FIG. 6 illustrates a front perspective view of the pouch 132. The pouch 132 may be made of material including nylon. The portable urinal 100 may be positioned inside the pouch 132. The pouch 132 has a rectangular bottom 133 with two flap toppers 133a embodying the portable urinal 100. On both sides of the pouch 132, there are two stretchable and durable net pockets to store the cover 126, the adjustable strap 135 and other accessories including small bottles or packets of sanitizer. On both top ends of the pouch 132, there may be a ring element 134 on each side for a removable and adjustable strap 135 to hook onto for carrying. The portable urinal 100 provides with only one set of the trap 135 used for both the pouch 132 and the container 104. These structures may, however, have any suitable design and coupling, and may be made of any suitable materials as shown in the first preferred embodiment.

The portable urinal 100 does not require the user to hold it nor attach it to any part of the user's cloth or body. It works best if the user positions its urine container 104 at a reasonable lower level, at least 2 or 3 feet below the user's genital for urine to flow steadily and smoothly without backing up. The user need not hold the container 104 nor the container 104 attached to the user's clothing. As long as the urine container 104 may be in a reasonably lower position than the user's genitals, the user can use the portable urinal 100 no matter what positions, standing, squatting, sitting or even lying or how close the urine stream may be to the inner wall of the receptacle body 123 as long as the urine streams are inside the sieve 125. At a shorter distance but still below the user's genital the user must manipulate the tube 102 to prevent backing up of the urine. The lid 121 of the receptacle 101 as mentioned above may be removable. These structures may, however, have any suitable design and coupling, and may be made of any suitable materials as shown in the first preferred embodiment.

In order to use the portable urinal 100, all its components must be connected properly. First the container cap 105 may be closed to the container 104. Then the fitting 123e of the receptacle 123 may be connected to the cap 116 of the tube 102, the fitting 117 of the tube 102 connected to the adapter 103a of the tube 103. After the user puts on a privacy garment 126, the container 104 may be left on a surface, the ground below the users' genital at least 2 or 3 feet and the receptacle 101 may be opened. By activation of the button 110 the latch 110a may be disengaged from its locking position. The control rod 109 drops down automatically and at the same time opens the cap 108 of the internally projecting tube 107. At this time the male user can urinate into the receptacle body 123. However the female user can remove the lid 121, positions the receptacle body 123 inside her underwear or slides her underwear to one side and applies the receptacle body 123 to her genitals then takes time to urinate into the receptacle body 123. With the sieve 125 there may be no urine splash back. After urination, the receptacle body 123 may be closed with its lid 121. The switch button 119*a* of the switch rod 119 may be pulled up to close the internally projecting tube 107 and the tube 102 may be wrapped up. The receptacle 101 may be then placed in the molded slot 131*a* and the privacy garment 126 may be placed either in the storage compartment 129 or in the side pocket of the pouch 132. Then the user can clean their hands with sanitizer. When filled the container 104 of the portable urinal 100 may be emptied and it may be ready for use again. These structures may, however, have any suitable design and coupling, and may be made of any suitable materials as shown in the first preferred embodiment.

When the need to use the portable urinal 100 is over, the user may put on a pair of medical gloves, and separate the receptacle 101 from the tube 102, the tube 102 from the adapter 103*a* of the tube 103 and opens the lid 121 from the receptacle body 123. The user then activates the button 110 to open the cap 108 of the internally projecting tube 107 and the circular protective cap may be screwed on to seal the round housing 106*a* from water and cleaning solution and remove the container cap 105. The privacy garment 126 may be removed for laundry wash. Then the urine may be drained into the toilet bowl. All the components of the portable urinal 100 are rinsed really well with water first. Then they are submerged in a pan of warm water mixed with such disinfecting and deodorizing cleaning solutions, as Odo-Ban©, Lysol© or bleach for half an hour. A bottle sponge or brush may be used to clean inside the container 104. Then all the components of the portable urinal 100 are rinsed really well with water again, allowed to dry and stored for next use. These structures may, however, have any suitable design and coupling, and may be made of any suitable materials as shown in the first preferred embodiment.

The Third Preferred Embodiment

The third preferred embodiment is modelled after the second preferred embodiment in a much more simplified way. It still uses the receptacle 101 as shown in FIG. 1 composed of the lid 121, the receptacle body 123, the neck 123*e* and the sieve 125, the urine transmission tube 102 as shown in FIG. 2 with the fitting 116 connected to the neck 123*e* and the fitting 117 connected to the adapter 302 of the new flow control assembly 300, also called a valve assembly, and the privacy garment 126 as shown in FIG. 5. For a full review of these components, please, consult the second preferred embodiment. For the scope of the third preferred embodiment many features of the new components are discussed and illustrated in the following.

This system is like the others mentioned above allowing a lot of people in developed and underdeveloped countries to use it where restrooms are inaccessible, remote or nonexistent or where some or many people are present without causing discomfort to them and without violating any local ordinances. It can also be used without being attached to a user's clothes or held by human body parts like hands or thighs. Most important, this system enables people with rheumatoid arthritis and osteoporosis who do not have to exert a good physical force by pulling or pushing a button to use it. The new flow control assembly takes care of their health problems by allowing them to use only the push function to open and close the portable urinal for use. It is a mechanical mechanism which achieves a full function automation.

Figure 9:
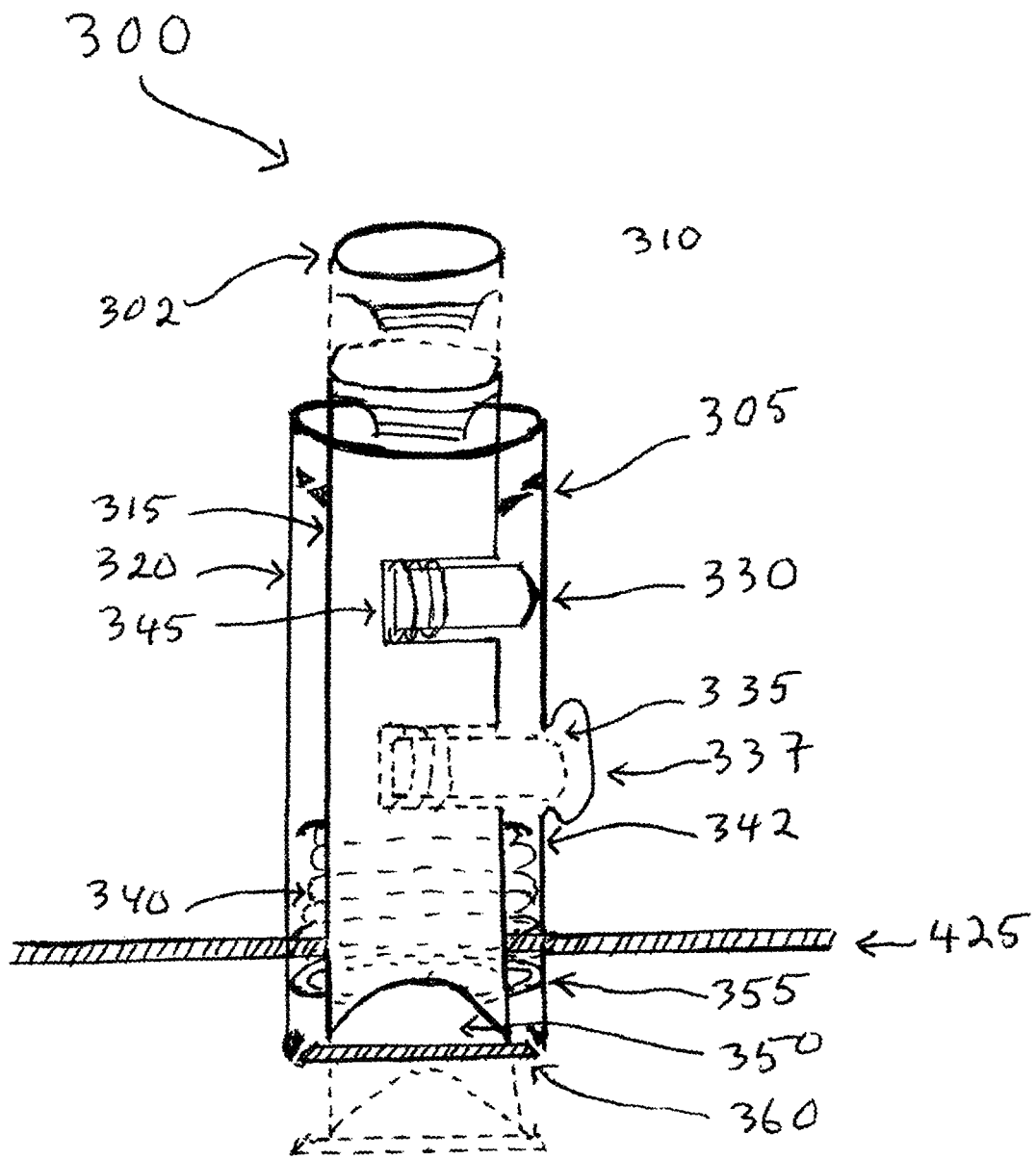
FIG. 9 is a schematic representation of the new spring-loaded flow control assembly using the urine pathway as an interior cylinder and the two springs enabling automation for both push and pull functions.

The new flow control assembly 300 as shown in FIG. 9 consists of an interior cylinder 315 and an exterior cylinder 320 positioned in a platform 425 sealedly connected to the container 400. All the components of the new flow control assembly are made of medical grade plastics except those are pointed out separately.

Figures 13, 14:
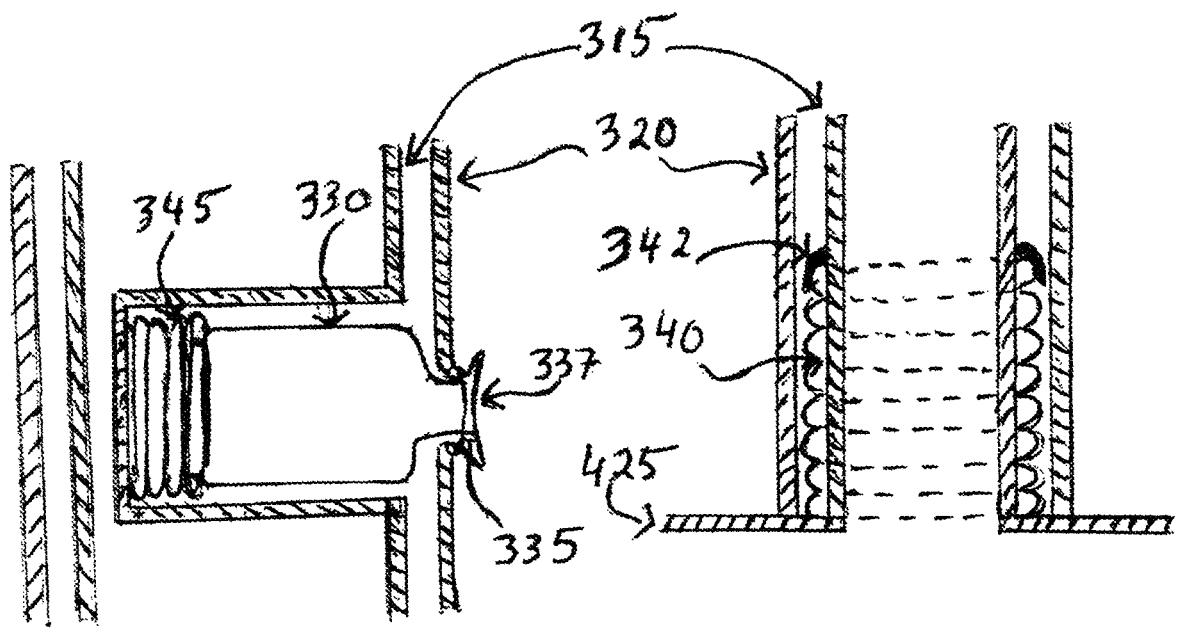
FIG. 13 shows a side-view of the spring and the function rod locked in the opening positioned on the exterior cylinder.
FIG. 14 shows the spring positioned on the platform held in check under the flaps between the interior and exterior cylinders.

The interior cylinder 315 is hollow inside and is used as a urine pathway. Urine is collected at the receptacle 101, transferred into the urine transmission tube 102 into the interior cylinder 315 and into the container 400. The interior cylinder has an adapter 302 on top connected to the fitting 117 of the urine transmission tube 102, a push button 310 below the adapter and a stop point 305 on both sides of the exterior wall of the interior cylinder as shown in FIGS. 11*a* and 11*b*. Below the stop point is a chamber which houses a spring 345 and a function rod 330 as shown in FIG. 13. Below the opening 335 there are two flaps 342 to hold the spring 340 in place as shown in FIG. 14. There is an O-ring 346 just below the platform 425 which holds tight to the exterior cylinder to stop bad odor and urine. At the bottom of the urine pathway are two openings 350 for urine to get out onto the container and a sealing member 360 used to close the urine pathway to the exterior cylinder. The sealing member is made of soft rubber and its edge is shaped in a 45 degree angle as shown in FIGS. 12*a* and 12*b*. The interior cylinder is movable in a vertical direction.

The exterior cylinder 320 wraps around the interior cylinder 315. Near the top it has 2 stop points 305 to stop the urine pathway to go far up. It has an opening 335 to engage and lock the top part of the function rod 330 in place. An opening cover 337 is used to hide the opening 335 as shown in FIG. 13. The bottom edge of the exterior cylinder 320 is shaped in a 45 degree angle as shown in FIGS. 12*a* and 12*b*. On the exterior wall of the exterior cylinder 320 half way up and half way down along the platform 425 is built with soft rubber. To position the new flow control assembly on the platform it is pushed in the slot where the soft rubber engages with the hard rubber built slot on the platform. The exterior cylinder is fixed in one position.

In the closed state, the push button 310 is ⅜" above the rim of the exterior cylinder 320. The function rod 330 is ⅜" from the opening 335. The spring 340 is 0.50" from the platform 325. The sealing member 360 is closed tight to the exterior cylinder 320 in a 90 degree angle. No bad odor or urine from the container 400 can get out. The portable urinal 100 is not in use.

In the open state, the push button 310 is pushed down ⅜", the interior cylinder 315 is also pushed down ⅜", the function rod is pushed down ⅜" and locked at the opening 335, compressing the spring 340 ⅜" down causing the sealing member 360 to a ⅜" lower position than the bottom edge of the exterior cylinder 320 creating an opening for urine to enter onto the container 400. The portable urinal 100 is in use.

FIGS. 11*a* and 11*b*, 12*a* and 12*b* illustrate the working relationship of both the top end and the bottom end of the new flow control assembly in the closed and open states.

Once done peeing the function rod 330 is pushed in, activating the spring 340 to push the function rod 330 upward ⅜" and stops at the stop points 305. As a result, the interior cylinder 315, the push button 310 and the sealing member 360 are pulled up ⅜". The open state returns to the closed state.

Figure 10:
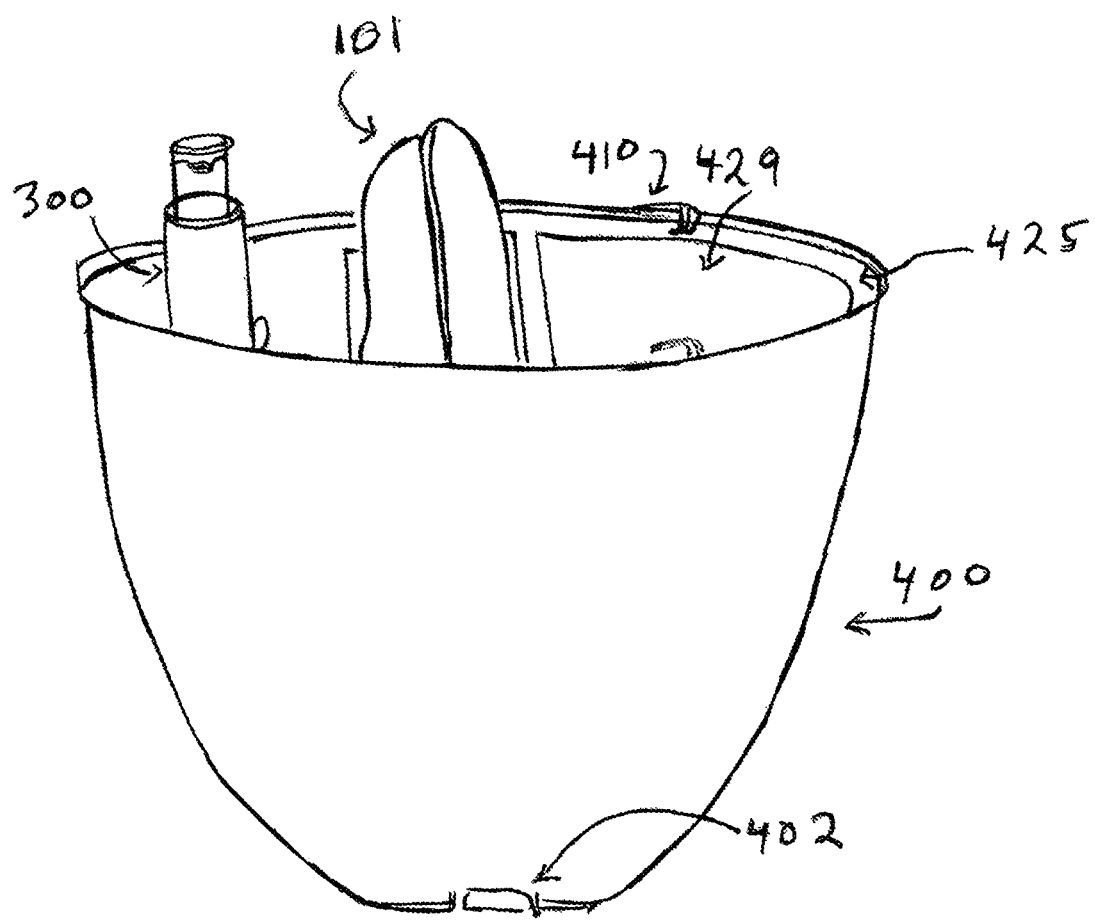
FIG. 10 illustrates the side view of the components neatly arranged on the platform of the container.

The container 400 has a cover 401 to close the container with such components as the new flow control assembly 300, the receptacle 101 and a storage compartment 429 for the privacy garment 126, the urine transmission tube 102 and small bottles or packets of sanitizer as shown in FIG. 10. The container 400 has a platform 425 sealedly connected to the top of the container 400 and a release opening 402 at the center of the container bottom.

On the platform 425 are positioned a slot for the new flow control assembly 300, one for the receptacle 101, a storage compartment for both the privacy garment 126 and the urine transmission tube 102 with a fastener 410 to hold both in place and a small space for small bottles or packets of sanitizer. The slot for the new flow control assembly is built with soft rubber to be locked onto the exterior cylinder. These are illustrated in FIG. 10.

Figures 15, 16:
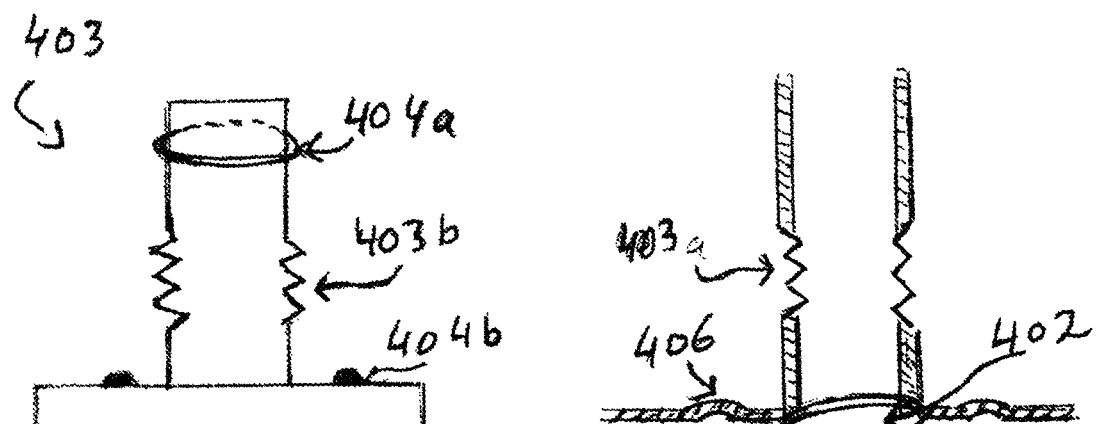
FIG. 15 illustrates the plug with an o-ring, some threads and another o-ring
FIG. 16 shows the release opening at the bottom end of the container with a groove, an opening and some threads.

The release opening 402 has a few threads 403a and a round hard plastic groove 406 just outside the release opening. There is a plug 403. The plug 403 first has an O-ring 404a, a few threads 403b and another O-ring 404b all used to seal off bad odor and urine inside. These are illustrated in FIGS. 15 and 16.

The new flow control assembly can be created with a ball instead of a function rod 330 with a spring 345 seated in the chamber within the interior cylinder and its working operation is exactly like that of the function rod. It can also be designed with the top part of the function rod positioned in another chamber created within the exterior cylinders. As the push button 310 is activated the function rod moves down the track and falls off the track and locks at the opening 335. The track should be built in a way that it cooperates with the push-in at the opening cover 337 and the reaction of the spring 340. However, the design with the function rod 330 in the third preferred embodiment is the best.

The portable urinal 100 in the third preferred embodiment is simple and compact. It is easy to use, easy to store and easy to care. Both the springs 340 and 345 are made of stainless steel. thus avoiding the problem of rustiness. The redesigning of the urine pathway 315 reduces cost by eliminating the urine tube 103 and many other components such as the wall 111, the control rod 109, the container cap 105 . . . and making the sealing member 360 much less cumbersome and much more efficient. The platform 425 has just about any components such as the flow control assembly 300, the receptacle 101, the privacy garment 126, the urine transmission tube 102 and packets of sanitizer needed for the job. It is so compact that it fits in a female handbag or any backpacks. But all of these are not the reasons for the redesign of the new flow control assembly. It is the people stricken with such health problems as rheumatoid arthritis and osteoporosis. The new flow control assembly 300 in the third embodiment is created to meet the needs of these health problem people. With the new flow control assembly 300 they do not need to exert any physical force with their fingers. All they need to do is to push the push button 310 to open and to push in the opening cover 337 to close the portable urinal 100. The flow control assembly 300 does achieve automation.

The cleaning of the portable urinal 100 may be a very important routine in using the portable urinal 100. The cleaning process is preferably started immediately after a day's use of the portable urinal 100. Decaying urine can cause corrosion and embed odor into the materials used to produce the portable urinal 100. Therefore, the cleaning process should not be delayed for more than 24 hours. The portable urinal may, however, be cleaned in any suitable manner or not at all. In an alternative embodiment the portable urinal may be made of antimicrobial, hydrophobic materials that do not require cleaning.

The portable urinal 1 of the first preferred embodiments, wherein a control rod is coupled to the closure and adapted to allow the user 17 to control the closure, wherein a weight 201 is attached to the control rod, such that the control rod moves automatically and opens the closure to the container 6 when the tube 8 is coupled to the container.

The portable urinal 1 of the first preferred embodiments, further comprising a stop 203 attached to at least one of the container 6 and the closure, wherein the stop prevents the movement of the closure beyond a given range of movement, wherein the stop is adapted to allow the closure to open sufficiently to allow easy passage of a flow rate of fluid 16 consistent with a stream of urine.

The second preferred embodiment is not intended to conflict with, nor be read as identical to the first preferred embodiment. The second preferred embodiment is intended to be enabling, and is not intended to limit the scope of the invention in any way.

The third preferred embodiment is also not in conflict with but identical in purpose to the first and the second preferred embodiments is intended to achieve automation beneficial to the health-problem people with rheumatoid arthritis and osteoporosis.

As a person skilled in the art will recognize from the previous detailed description and from the figures and claims, modifications and changes can be made to the preferred embodiments of the invention without departing from the scope of this invention defined in the following claims.

I claim:

1. A portable urinal assembly comprising:
   a receptacle including an opening, a rim, and a receptacle outlet neck; wherein the rim is surrounding the opening;
   a urine tube having a first end and a second end, the first end being configured for coupling to the receptacle outlet neck;
   a urine container having a urine container cap;
   a valve assembly comprising:
   (i) an interior cylinder slidably received in an exterior cylinder, the interior cylinder having an interior cylinder top end and an interior cylinder bottom end, the interior cylinder top end including an interior cylinder top end adapter, which being connected to the second end of the urine tube; wherein the interior cylinder bottom end has one or more urine holes configured to let urine flow into the urine container;
   (ii) the exterior cylinder having an exterior cylinder top end and an exterior cylinder bottom end; the exterior cylinder bottom end being mounted to the urine container cap;
   (iii) a button release being located proximate the interior cylinder top end;
   (iv) an interior sealing member extending around the interior cylinder bottom end and an exterior sealing member being installed on an interior surface of the exterior cylinder; wherein
      (a) in a closed position, the interior cylinder bottom end and the exterior cylinder bottom end are adapted to be adjacent each other, and the interior sealing member is adapted to be in direct contact with the exterior cylinder bottom end to prevent the urine from exiting the valve assembly;
      (b) in an open position, the interior cylinder bottom end is adapted to be located below the exterior cylinder bottom end such that the interior sealing member is not in contact with the exterior cylinder bottom end; and the one or more urine holes are open to the urine container; and (c) in the closed position and in the open position, the exterior sealing member is configured to stop leakage of odor and the urine between the interior cylinder and the exterior cylinder;

(v) a function rod and a first spring which are housed in a cylindrical chamber located in the interior cylinder; wherein the first spring is located at an end of the function rod and a second spring is positioned between the interior cylinder and the exterior cylinder; and wherein (a) when the button release is pushed down, the function rod moves downwardly, and aligns with a function rod hole on the exterior cylinder, the first spring pushes the function rod into the function rod hole and holds the function rod inside the function rod hole for the open position;

(b) when the function rod is pushed in from a function rod hole cover on the exterior cylinder, the function rod is completely out of the function rod hole, the second spring pushes the interior cylinder including the function rod upwardly for the closed position; and (vi) a urine pathway; wherein the urine pathway is located inside the interior cylinder, and runs from the interior cylinder top end adapter to the interior cylinder bottom end; and wherein the urine runs through the urine pathway and outside the cylindrical chamber, is allowed to flow through the urine pathway by the valve assembly in the open position, and is disallowed to flow by the valve assembly in the closed position;

wherein in the open position the urine is allowed to flow without interruption from the receptacle through the urine tube and through the urine pathway into the urine container; and wherein in the closed position the urine is disallowed to flow and secured in the urine container.

2. The portable urinal assembly of claim 1, comprising a privacy garment; wherein the privacy garment has openings and strings; the openings are adapted to provide access to inside of the privacy garment and the strings are adapted to be wrapped around a user's waist and wherein the privacy garment is configured to be worn in public.

3. The portable urinal assembly of claim 1, wherein the receptacle is shaped to fit a female user's genital in front and is rounded in the rear for male users; wherein the rim is covered by a silicone polymer cushion.

4. The portable urinal assembly of claim 3, wherein the receptacle further includes a removable receptacle lid configured to be sealably secured to the rim.

5. The portable urinal assembly of claim 1, wherein the receptacle further comprises at least one of a sieve, and a mesh located in a cavity of the receptacle; and wherein the sieve is configured to prevent urine splash-back onto a user.

6. The portable urinal assembly of claim 1, further including a storage portion which includes a sealable cover.

7. The portable urinal assembly of claim 1, wherein the urine container includes a release opening; wherein the release opening has a sealing member and male threads to engage with female threads; and wherein the release opening permits the urine to be drained out of the urine container by a user.

8. The portable urinal assembly of claim 1, wherein the second spring is a coil spring.

9. The portable urinal assembly of claim 1, wherein the interior sealing member and the exterior sealing member comprise one or more O-ring seals.

10. The portable urinal assembly of claim 1, wherein (1) the interior cylinder includes the cylindrical chamber orthogonal to an axis of the interior cylinder and extending inwardly from an exterior surface of the interior cylinder; (2) the exterior cylinder includes the function rod hole extending through an exterior cylinder sidewall; (3) a releasable locking mechanism comprises the button release and the function rod; wherein the function rod is outwardly biased by the first spring for locking the valve assembly in the open position.

11. The portable urinal assembly of claim 10, wherein the function rod hole is covered by the function rod hole cover on the exterior cylinder.

12. The portable urinal assembly of claim 10, wherein the function rod is biased against an interior surface of the exterior cylinder when in the closed position.

13. A method of using the portable urinal of claim 1, the method comprising:

connecting the receptacle outlet neck to the first end of the urine tube;

connecting the second end of the urine tube to the interior cylinder top end adapter of the valve assembly;

installing a sieve in a cavity of the receptacle;

removing a privacy garment from inside a storage portion pushing down the button release to move the function rod downwardly; the first spring pushes the function rod into the function rod hole for the open position;

donning the privacy garment with strings being wrapped around a user's waist;

positioning the receptacle proximate the user's genitalia;

urinating into the receptacle;

pushing the function rod inwardly from the function rod hole cover to force the function rod completely out of the function rod hole; the second spring pushes the interior cylinder upwardly for the closed position;

taking off the privacy garment;

storing the receptacle, the urine tube and the privacy garment inside the urine container lid.

* * * * *